United States Patent [19]

Dout et al.

[11] 4,129,122

[45] Dec. 12, 1978

[54] PATIENT ISOLATION ROOM WITH LAMINAR FLOW FEATURE

[75] Inventors: James A. Dout, Fullerton; Robert E. Foreman, Santa Ana, Calif.

[73] Assignee: Sterilaire Medical, Inc., Santa Ana, Calif.

[21] Appl. No.: 791,419

[22] Filed: Apr. 27, 1977

[51] Int. Cl.$^2$ .............................................. A61B 19/00

[52] U.S. Cl. ........................................ 128/1 R; 98/36

[58] Field of Search ............... 128/1 R, 1 B, 139, 204, 128/298; 98/33 A, 36; 21/74 R; 55/340, DIG. 29; 52/205, 204, 172

[56] References Cited

U.S. PATENT DOCUMENTS

| | | | |
|---|---|---|---|
| 2,075,065 | 3/1937 | Ish-Shalom et al. | 52/204 |
| 2,104,024 | 1/1938 | Conboie | 98/33 A |
| 3,084,684 | 4/1963 | Saunders | 128/1 B |
| 3,143,952 | 8/1964 | Simons | 98/36 |

OTHER PUBLICATIONS

Agnew, Laminar/Flow Clean Room Handbook, 1965, pp. 1-25.

*Primary Examiner*—Henry J. Recla
*Attorney, Agent, or Firm*—Louis J. Bachand

[57] ABSTRACT

A patient isolation room having walls surrounding a relatively smaller patient locus, with continuous air flow loop including an air inlet and outlet relatively sized and oppositely arranged to encompass the patient locus on every side with a horizontal, unidirectional, laminar air stream of uniform velocity throughout its cross-section to maintain patient isolation from room air beyond said locus, the loop conducting depurified air beyond the room for recirculation and repurification.

9 Claims, 8 Drawing Figures

PATIENT ISOLATION ROOM WITH LAMINAR FLOW FEATURE

BACKGROUND OF THE INVENTION

This invention has to do with patient isolation rooms, and more particularly, is concerned with improvements in known patient isolation rooms whereby the patient is maintained isolated from room air beyond the patient locus so that the patient is not exposed to potentially bacteria- and/or virus-contaminated air carried by hospital personnel or others co-present in or about the room with the patient. Apparatus is provided to achieve horizontal, unidirectional, laminar air stream flow of uniform velocity throughout its cross-section linearly across the patient locus, whereby cross-streams such as may be present in prior known rooms, which cross-streams may carry bacteria- and/or virus-contaminated air across the patient locus, are obviated.

For effective care of patients undergoing physically debilitating treatments such as chemotherapy to ameliorate cancerous conditions, and others especially susceptible to infection, such as burn victims, it is essential to isolate the patient as much as possible from sources of infection. Conversely, it is desirable to protect hospital personnel from infectious patient conditions. For these purposes, there have been developed "isolation rooms" which are spaces within the hospital having controlled air sources and which generally are operated under a positive pressure to exclude contamination to the maximum degree. Some of these rooms provide accordian folding walls equipped with viewer isolating viewports and associated hand glove ports for care of the patient while providing nearly total isolation from infection. State of the art viewports, however, are curved at critical areas, giving an optically distorted view of the patient. This invention provides a solution to this problem. Further, the present invention relates to virustatic control for patient isolation rooms.

PRIOR ART

As presently known, isolation rooms in hospitals are constructed to have at one end wall a bank of High Efficiency Particulate Air filters, termed HEPA filters in the art, which are arranged in a bank of vertical and horizontal rows of filters. A blower as a source of pressurized air is provided to force air to be purified, e.g. bacteria purged, through the HEPA filters. The air stream, as thus purified, is wafted across the bed defining the patient locus, and then recovered for recirculation. Recovery of the purified air leaving the patient is necessary for filtration economy, but has been a problem. In one form of the isolation room, there is provided outside of the room itself an air return system comprising a gross, non-HEPA filter leading to the intake of the blower being used to pressurize air for passage through the HEPA filters. Generally, these air circulation systems use the room doorway as an air outlet passage. This arrangement is deficient in at least two significant respects: The location of the patient's bed is often adjacent the viewport sidewall so that the patient may be most easily treated, and the corner doorway therein becomes the air outlet. All airstreams emanating from the HEPA filter bank are funnelled toward that doorway corner. When a doctor or other medical person is within the room and next to the patient's bed, the cross current, which is produced by the room air flow narrowing from the width of the filter bank wall to the width of only a doorway of the room, carries the bacteria and/or virus contaminants of the doctor or other hospital person across the patient locus, defeating the isolation function of the room. Even standing in the doorway sets up eddies and backwash air flows which can carry contaminants back into the room, although the air flow is primarily out the door. The corner doorway outlet arrangement is further deficient because of the resultant inability to maintain closed the doorway to the room. Children have been known to wander through an open doorway and leave the room. Use of half-doors has been tried to block the child's egress, but this expedient likewise blocks full air flow through the outlet, since the half-door acts as a baffle, increasing the funnelling effect experienced at the door opening, and doubling intended outlet air flow from 300 to 600 feet per minute. Moreover, no door, or only a one-half door, precludes protection of hospital personnel from contagious patient conditions, since the depurified air stream is unconfined at the doorway and may pervade other hospital spaces.

SUMMARY OF THE INVENTION

It is, accordingly, an object of the present invention to provide an improved patient isolation room. It is a further object to provide a patient isolation room in which air flow is horizontal, unidirectional and laminar and of uniform cross-section velocity throughout the patient locus. It is yet another object to provide a patient isolation room in which horizontal, unidirectional and laminar purified air streams encompass the patient locus on every side, linearly and without cross-streams, and thus without contamination of the patient locus by doctors or hospital personnel present in the room. Yet another object is to provide a patient isolation room in which the air inlet-outlet system permits the room door to be closed without blocking air recirculation through the room, thus obviating eddying and other turbulences about the doorway and their concomitant contamination. It is a further object to provide a more economical isolation room construction through the use of overhead air recirculation; and, with air recirculation which is quieter in use than patient isolation rooms heretofore known. It is a still further object of the invention to provide a more highly purified air stream to the room through the elimination of viral e.g. influenza contaminants as well as bacterial agents. It is a further and highly advantageous object to provide apparatus for the repetitive and automatic virustatic conditioning of the air stream during recirculation to and from the patient isolation room. It is another object to virustatically treat humidifying water to be passed into a patient isolation room, thereby controlling another source of difficulty in operation of such rooms, and as well to render HEPA filterable the viral agents, if any, within the air which are not normally so filterable.

These and other objects of the invention are realized in accordance with the apparatus hereinafter described, which comprises, in general, a patient isolation room having side, top and bottom walls surrounding a relatively smaller patient locus, and continuous air flow loop means isolating said locus from airborne contaminants beyond the locus, the loop means within the room including an inlet and outlet relatively sized and oppositely arranged to encompass the patient locus on every side with a purified, horizontal, unidirectional laminar air stream of uniform velocity throughout its cross-section, the loop means beyond the room conducting depurified air from the loop outlet above the room top wall for repurification and recirculation. Typically, the air flow loop means further includes the room air inlet being adjacent the patient locus, and an air purifying filter means adapted to pass purified air to the inlet for horizontal, unidirectional, laminar, cross-sectionally uniform flow therefrom toward the locus. The air flow loop means room air stream outlet is typically adapted to draw the air stream entering at the room inlet horizontally and unidirectionally across the patient locus to define with the inlet the mentioned locus encompassing relation. Further, the air flow loop means may include a blower beyond the room in air-drawing communication with the room outlet and in pressurized air communication with the room inlet.

In preferred embodiments, the air flow loop means includes a portion defining a closed passage above the room top wall receiving and passing across the top of the room contaminated or depurified air streams recovered from the room, in isolated relation for repurification and recirculation. The air stream outlet in such embodiments may comprise a first wall port spaced above the plane of the room bottom wall and horizontally and vertically extended to receive the horizontal air streams traversing the patient locus in the noted encompassing relation.

There may be provided a high efficiency, particulate air (HEPA) or other effective filter means in the air flow loop means, the air stream inlet comprising a second wall port adjacent the patient locus in air filter communicating relation with the filter means; the room air inlet port and outlet port being respectively horizontally and vertically extended, e.g. the inlet port being approximately commensurate with the air filter means, and opposed across the interior of the room, to traverse the patient locus with a purified air stream dimensioned to continuously encompass the locus on all sides during air stream passage between the inlet wall port and the outlet wall port.

In particular embodiments, the outlet first wall port is formed in a room side wall and the second inlet wall port is formed in the side wall opposite the outlet wall, to define the opposed relation of the inlet wall port and the outlet wall port. Alternatively, the outlet, first wall port may be formed in the room top wall (or ceiling) and the second, inlet wall port in the room side wall beyond the patient locus, relative to the first, outlet wall port, to define the opposed relation of the inlet wall port and the outlet wall port.

Further features of the apparatus include foreclosing room contamination from the closed passage above the room from dust and other contaminants above the room ceiling indraughted through spaces between ceiling panels, by having the room and closed passage dimensioned to have the air stream volume within the room and the closed passage (below the room top wall) flow as an air stream of lower velocity within the room which is of course thus relatively larger in volume, than the air stream beyond the room above the top wall (in the closed passage), which is of course thus smaller, relatively, in volume, the net effect being to draw contaminants upward from the room through any leakage points in the top wall by Venturi action, the Venturi action acting against room contamination from the passage through the room top wall.

Together with these features, the apparatus in its preferred embodiments also includes, as in other embodiments, in the loop means: an air blower communicating negative pressure to the room outlet wall port through the closed passage and positive pressure to the inlet wall port through the air filter; in the room: the outlet first wall port, being formed in a room side wall, and the second, inlet wall port, being formed in the room side wall opposite the outlet wall port to define the opposed relation of the inlet wall port and the outlet wall port; and withal the room and closed passage being relatively dimensioned to have a lower velocity air stream within the room below the top wall than beyond the room against room contamination from the passage through the room top wall.

Still other features include the patient locus being immediately adjacent a room side wall free of inlet and outlet wall ports, and the invention apparatus providing a viewport positioned in this locus-adjacent wall in patient viewing relation for a viewer outside the room, the viewport comprising an inwardly projecting panel assembly including a first, transparent planar panel extending angularly upward from the room wall a distance to provide a nonaberrant view downward of a patient within the patient locus, and at least one additional panel supporting the first panel in its position on the wall in viewer isolating relation.

Yet another feature of the herein disclosed apparatus is the distributive provision of a supply of virustatic material, and air pervious reticular structure positioned across the air flow path within the loop carrying the material supply in labyrinthine relation for random and repeated contact with air flowing in the loop to control virus in air flow loop air. In particular embodiments, the air flow loop means may further include a humidifier adapted to generate moisture vapor for entrainment in the loop air flow by water assisted evaporation of stored water, and the apparatus include also a biostatic material supply, and means to meter the supply material into the stored water to control virus and bacterial growth in the stored water.

BRIEF DESCRIPTION OF THE DRAWINGS

The invention will be further described as to illustrative embodiments thereof in conjunction with the attached drawings, in which.

DESCRIPTION OF THE PREFERRED EMBODIMENTS

System Overview

In each of the several embodiments now to be described, a blower-pressurized bank of HEPA filters is the source of a "piston" of purified air which moves through the patient locus laminarly, unidirectionally, horizontally and with uniform velocity throughout its cross-section. In each embodiment, an outlet for the air so moving is provided in a size, configuration and location relative to the HEPA filter bank as to enable the just described air movement. Between the air inlet and air outlet a wall-less passage is defined free of pinching or funneling effects and the patient locus is encompassed within this passage, thus isolated by the air curtain effect of the air stream flow at the peripheries of the patient locus. In each embodiment, the air is captured in a negative pressure outlet in the ceiling or in a room vertical wall outlet and carried back to the HEPA filter bank, with blower repressurization, and optionally viral conditioning and gross filtration, through a closed or walled passageway provided at least partially above the isolation room ceiling.

First Embodiment

Figure 1:
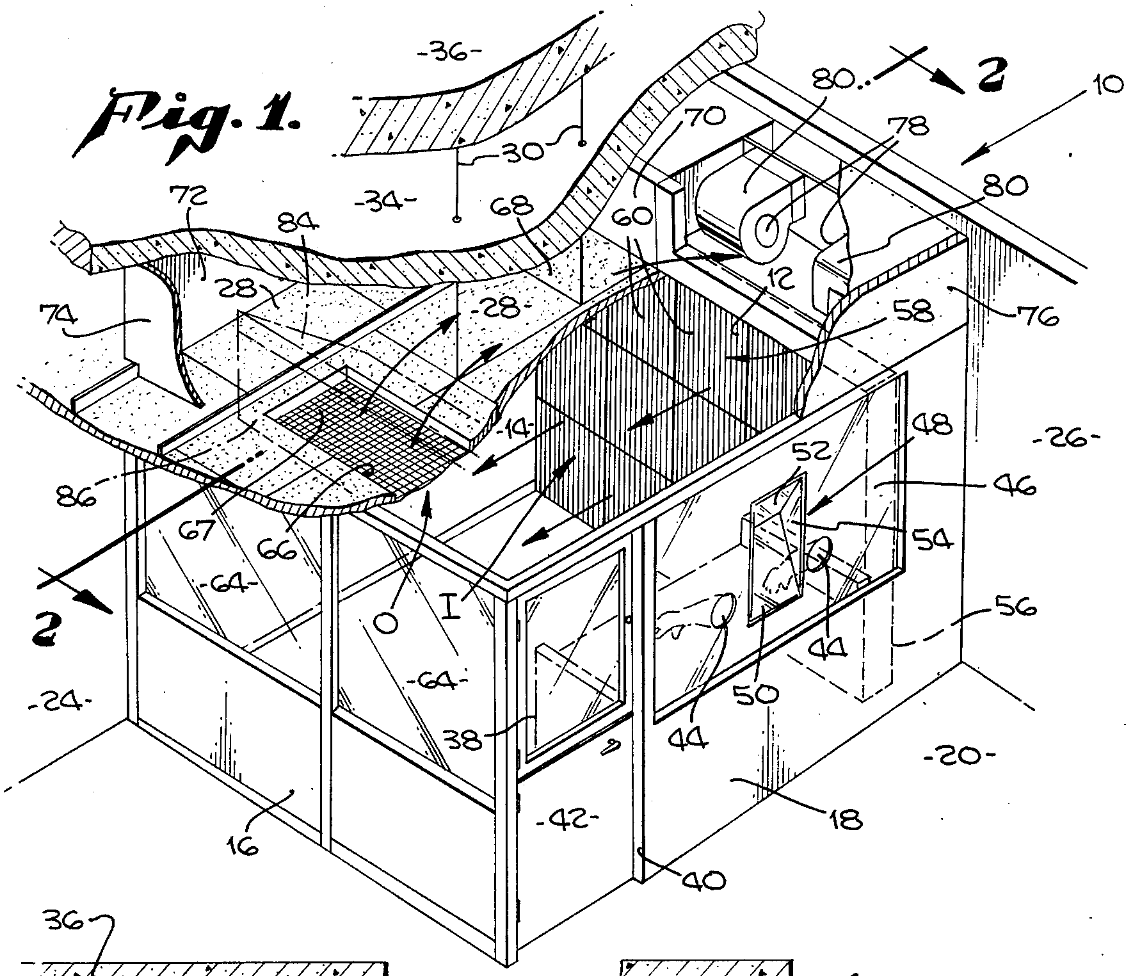
FIG. 1 is a perspective view of one form of patient isolation room according to the invention, featuring a top mounted blower and a ceiling air outlet to a loop air flow passage above the room.
Figure 2:
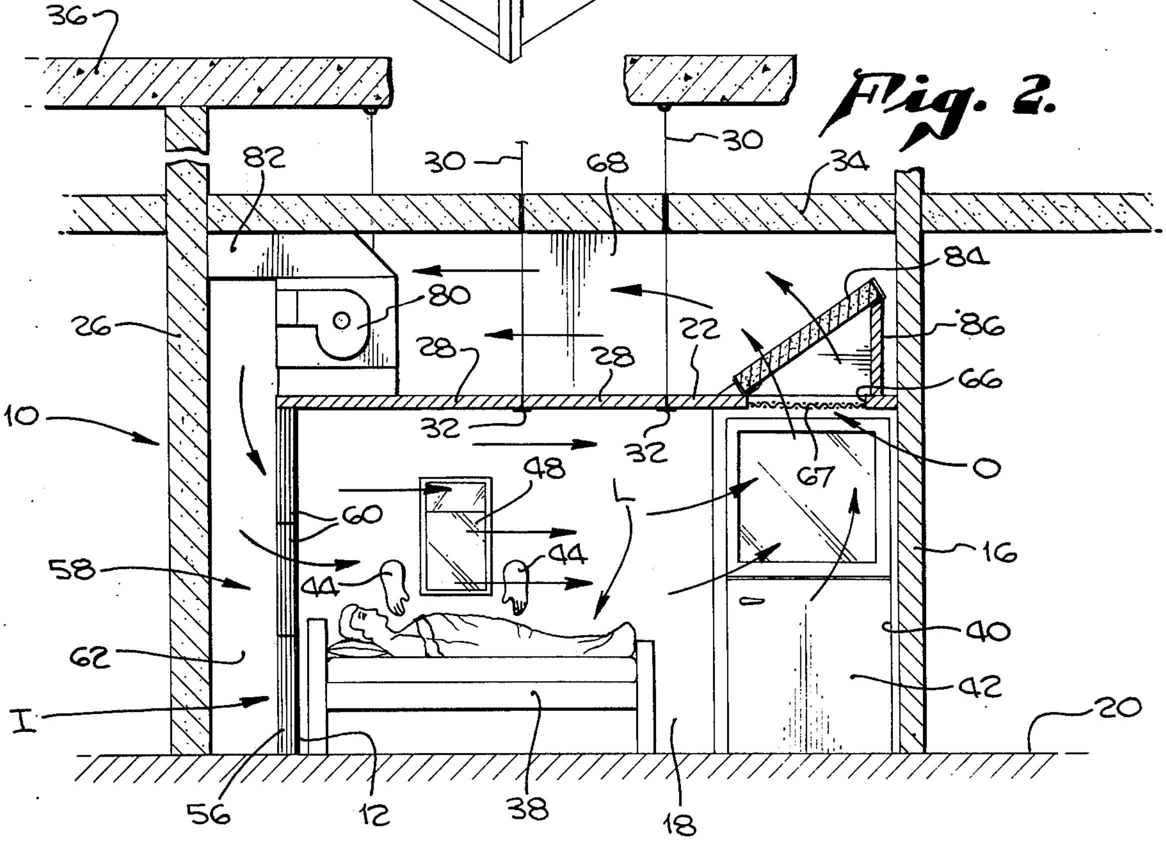
FIG. 2 is a side view in vertical section thereof.

With reference now to the drawings in detail, the first embodiment is shown in FIGS. 1 and 2. This first embodiment is characterized by a ceiling air outlet or return, an overhead blower installation, and an improved type of viewport according to the invention. Thus the patient isolation room 10 is seen to comprise four rectangular vertical walls 12, 14, 16 and 18, a horizontal bottom wall 20 as a floor and a horizontal top wall 22 as a ceiling. Room 10 is typically set up inside an existing hospital room on an existing hospital corridor. Thus hospital room walls, e.g. walls 24, 26 and others not shown may enclose the patient isolation room 10. The room 10 ceiling is formed of rectangular plastic panels 28, supported by a tie bar 30 and grid 32 arrangement, below the normal hospital room plaster ceiling 34 which in turn is below the structural reinforced concrete flooring 36 for the next story of the hospital building. Thus the patient isolation room 10 is set up apart from other hospital spaces.

The locus L of the patient in the room 10 is determined by positioning of bed 38. Conventionally for cancer victims this location is as shown in FIGS. 1 and 2, alongside side wall 18. Burn victims may be desirably positioned alongside wall 12.

Wall 18 may be in a hospital corridor or within a larger room space and is shown to include a doorway 40, a split door 42, a pair of glove ports 44 carried by a flexible transparent member 46 for translational movement. A viewport 48 is also provided, carried by member 46 in wall 18. Viewport 48 comprises a first planar transparent panel 50 extending upwardly and inwardly from member 46 to provide an untrammelled and nonabberant view of the patient in locus L by virtue of the planarity of the viewport in the line of vision of the person outside the room to the patient. Old style "bubbles" were shaped like airplane cockpit canopies and were curved at the critical intersection with the normal line of sight and gave distorted images. A second and shorter upper panel 52 and side panels 54 support the view panel 50 in its place on the member 46 and complete the viewport assembly.

Figure 5:
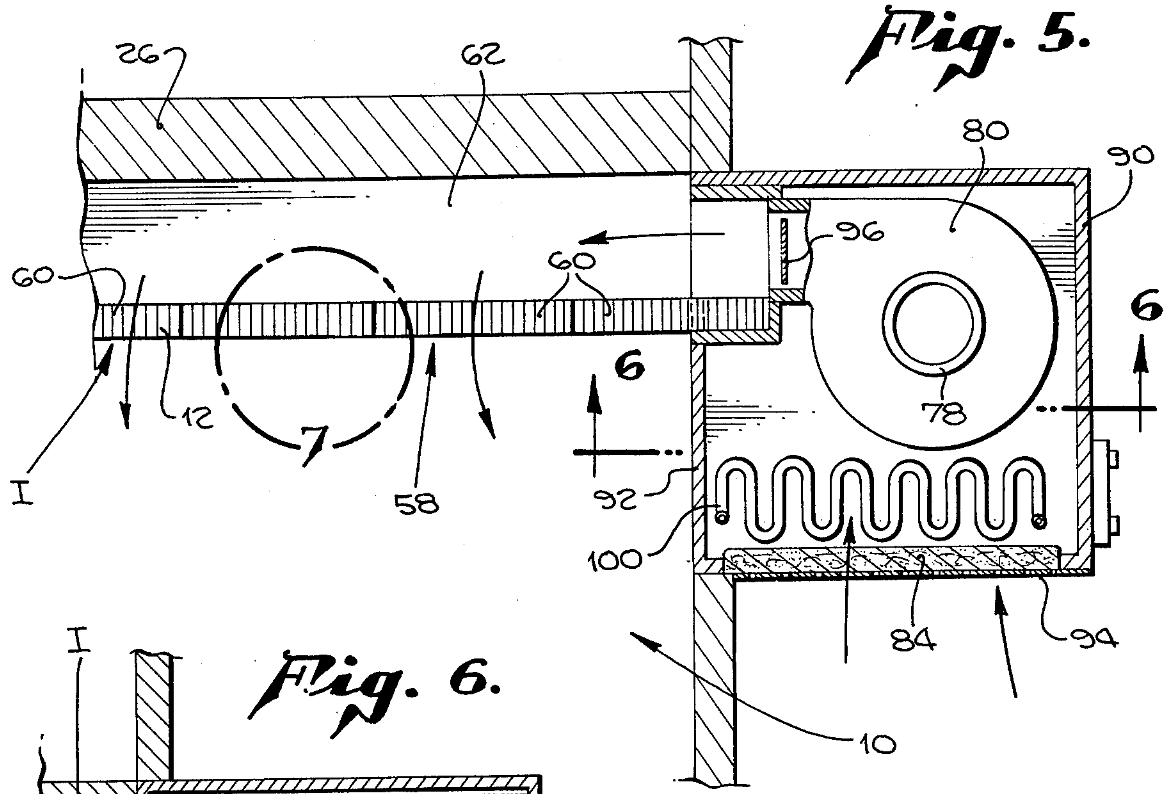
FIG. 5 is a detail view, greatly enlarged, of the recirculating air blower system taken on line 5—5 in FIG. 4.
Figure 7:
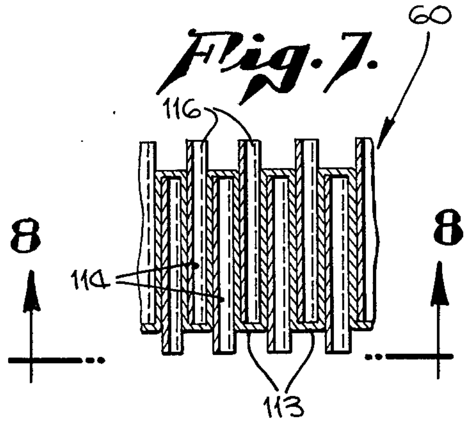
FIG. 7 is a detail horizontal section view of the HEPA filter element, greatly enlarged, taken on line 7 in FIG. 6.
Figure 8:
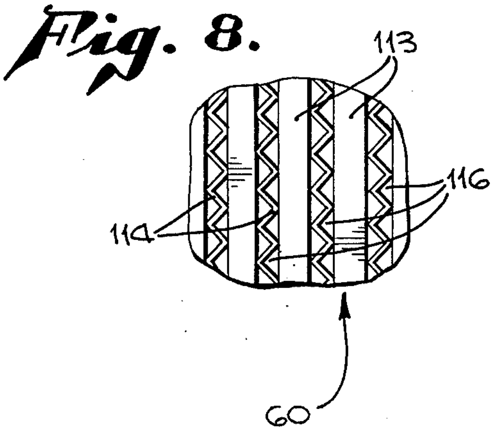
FIG. 8 is a front plan view of the HEPA filter element taken on line 8—8 in FIG. 7.

Wall 12 forms one end of the room 10 and comprises a perimetrical frame 56 which encloses and supports a bank 58 of HEPA filters 60, shown in structural detail in FIGS. 5, 7 and 8. Wall 12 is spaced from hospital room wall 26 to define a plenum 62 for purposes to be described, and defines a room air inlet port I commensurate with the extent of the HEPA filter bank 58.

Walls 14 and 16 complete the vertical walls of the room 10 and may be plain or windowed at 64 as shown. Bottom wall 20 is typically the conventional hospital flooring.

Top wall 22 is the room ceiling as noted earlier, and in this embodiment of the invention it is provided with a generally rectangular opening 66 into which a reticulated grill 67 is inserted. The opening 66 defines a room air outlet port 0 commensurate with the opening. It will be noted that the outlet 0 (opening 66) is oppositely arranged to the inlet I (filter bank 58) across the patient locus L (bed 38) and that air streams entering at I will traverse the locus L and encompass the locus on every side in passing to the outlet 0.

Above the room ceiling or top wall 22 a closed passage 68 in communication with opening 66 is defined by the normal plaster ceiling 34 above, and room wall skirts 70, 72, 74 and 76 which peripherally enclose the above ceiling space as the room walls 12, 14, 16 and 18 do below the ceiling. Skirts 70–76 are not necessarily or even preferably continued extents of the room walls 12–18 but may be of any arrangement defining the closed passage 68 as a space of less volume than room 10 for purposes mentioned herein. Also in communication with the closed passage 68 are the intakes 78 of blowers 80. Blowers 80 are mounted on framing 82 above the plenum 62 and arranged so as to exhaust blower pressurized air into the plenum (see FIG. 2). Thus arranged, the blowers 80 indraught air in the closed passage 68 from opening 66, which is possibly depurified or "contaminated" by passage through the room 10, by inducing a negative pressure in the passage 68 as though the passage were an extension of the blower inlet. This negative pressure draws air into opening 66 within room 10. The filter bank 58 is in open communication with plenum 62 which it will be observed is at a super pressure. Air passes through the filter bank 58 with a pressure drop typical of HEPA filters and across the patient locus L under the influence of opening 66 whereby the inlet I and outlet O cooperate to pass the air stream across the locus in unidirectionally laminar relation, and at a uniform velocity in cross-section throughout locus L. Beyond the locus L the air streams tend upward and enter the opening 66 (see arrows FIG. 2). It is noteworthy that the substantial horizontal extent of the opening 66 enables air stream traversal of the patient locus L without lateral pinching or a horizontal cross-current, obviating non-linear air flows which can cause carriage of contaminants from beyond the locus into the locus.

Note to that the door 42 is kept closed during room operation, eliminating child wandering, eddies and backward currents from doorway standing of personnel, and contamination of hospital corridors and other spaces with room air, and enabling facilitated air conditioning and purification performance in a closed system.

A supplemental filter 84 supported by framing 86 is provided downstream of the ceiling opening 66. This filter 84 is typically of low efficiency and made of polyester or other fibrous mat; its purpose is to prolong the life of the high efficiency HEPA filters by screening out gross contaminants such as dust. In a further aspect of this invention, filters such as filter 84 may be used to define an air pervious structure which may be coated as to its individual fibers with a persistant quaternary ammonium compound or mixture of such compounds such as that sold under the trade name Control III which are demonstrated virustatic compounds. Thus coated, and recalling the labyrinthine path through a mat of such fibrous material, the filter 84 describes an intricate maze for air flow, virus carried in the air will collide randomly and repeatedly with the fiber coating, being killed or deactivated in the process whereby the air leaving the filter 84 is purified of live virus. Bacteria, of course, will likewise be killed, but these are of less concern since the HEPA filters 60 are able to filter out bacteria before the recirculated air is returned to the room 10.

It is additionally to be noted that the volume of closed passage 68 being less than the volume of room 10, and the quantum of air flowing through each being the same, that the velocity of air in the passage is greater than in the room. Thus any surface air flow effects along the ceiling, e.g. Venturi suctions will tend to draw air upward between ceiling panels 28 and grid 32 so that dust, dirt and plaster accumulations and bacterial contaminants in the passage 68 are not drawn downward into the room.

Second Embodiment

Figure 3:
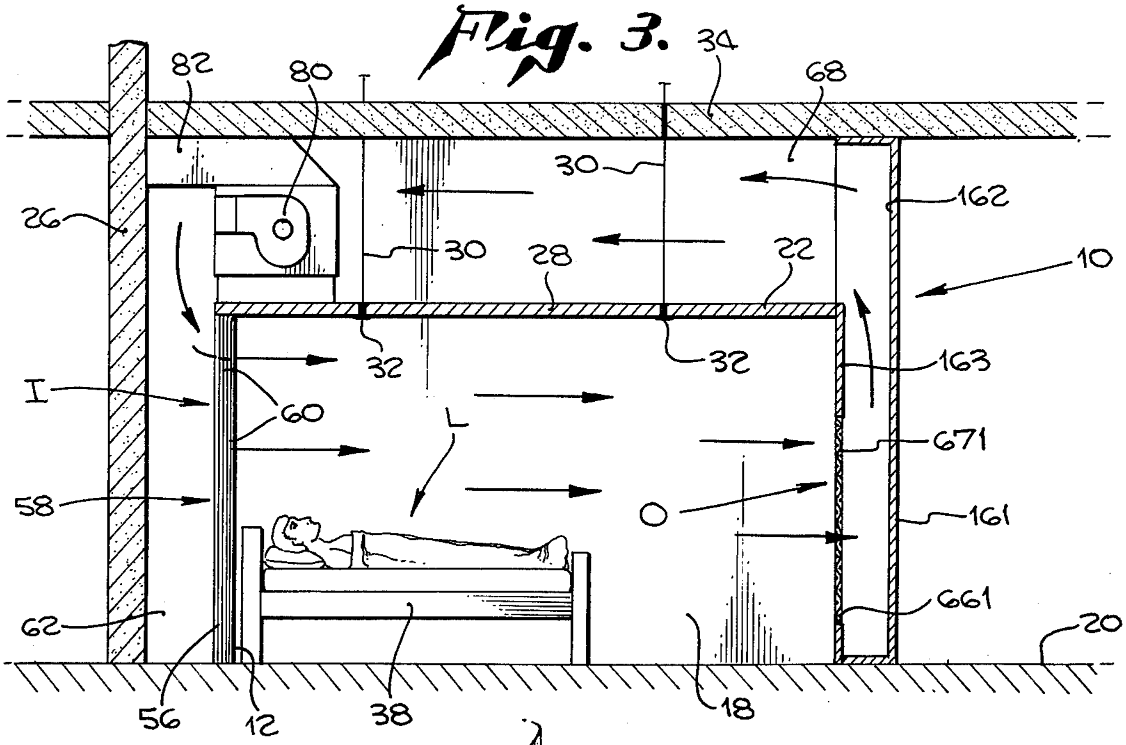
FIG. 3 is a view like FIG. 2 of another form of the invention featuring an end wall air outlet to the loop flow air passage above the room.

Turning now to the embodiment of FIG. 3, the room 10 arrangement is similar to FIGS. 1 and 2 except that in this embodiment the end vertical wall 16, noted as wall 161, is modified to comprise front and rear elements, the rear element 162 being solid and the front element 163 having an opening 661 formed therein, analogously to opening 66 in ceiling 22 of the FIG. 1 embodiment, and likewise provided with a grill 671 to define outlet port O. In the FIG. 3 embodiment, the air passed into the room 10 by HEPA filter bank 58 traverses the patient locus L flowing in a horizontal, laminar and unidirectional manner and encompassing the locus on every side, the outlet port 0 being so constructed and arranged as to horizontal extent (width) and height per se and of spacing above the plane of floor 20 relative to the inlet port I (the bank 58) and the locus L (bed 38) that the air piston envelopes the bed continuously and linearly. The FIG. 3 embodiment is shown to employ the overhead mounted blower 80, but a side-mount blower may be used with appropriate alterations in the closed passage 68 as in FIG. 4 now to be described.

Third Embodiment

Figure 4:
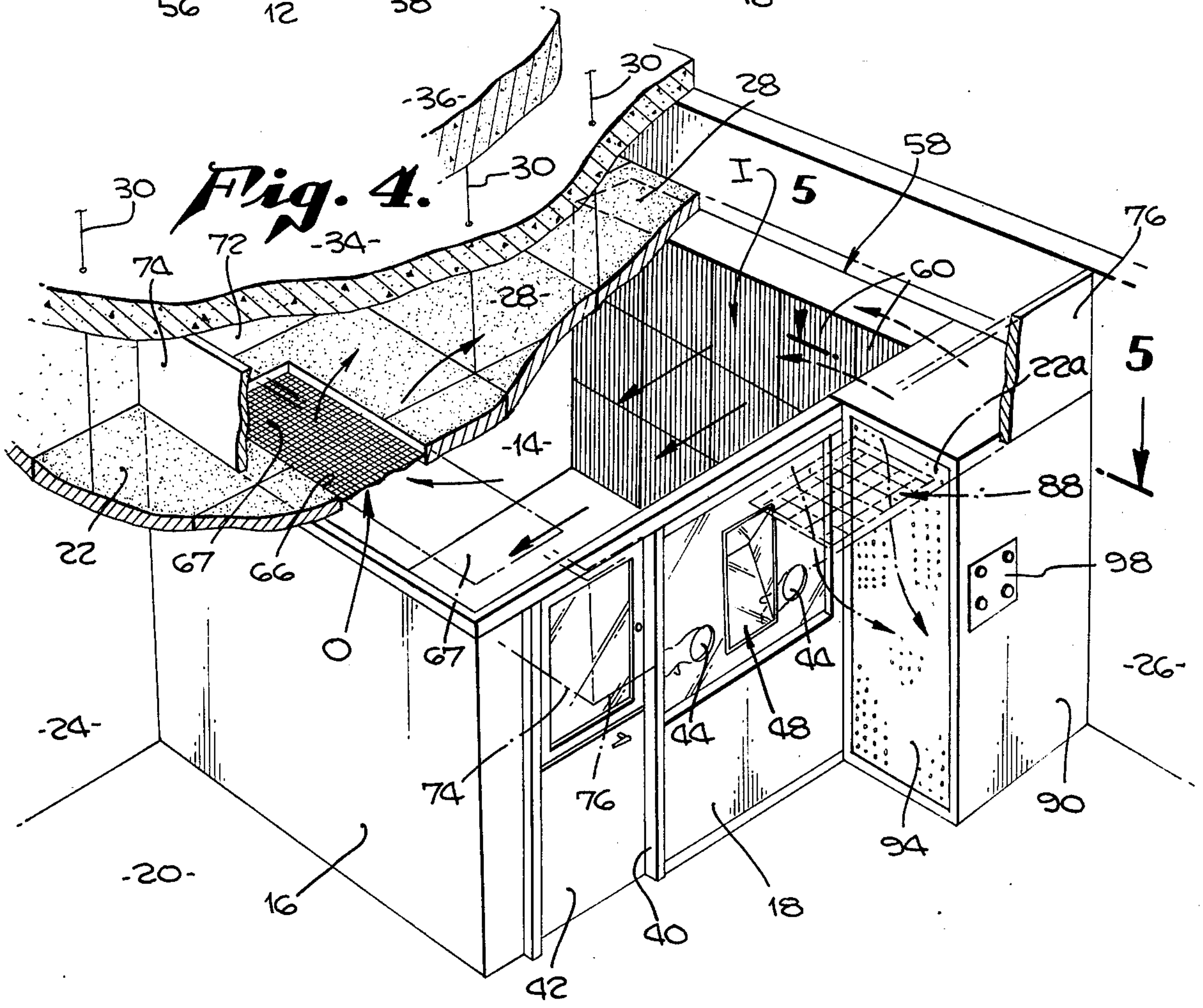
FIG. 4 is a perspective view of the presently preferred alternative embodiment of the invention, featuring a side mounted blower and the ceiling air outlet to a loop flow passage above the room and to the blower.

The embodiment of FIG. 4 is the currently preferred form of the invention because of the ease of installation and the present state of the art of side-mount blowers. In this embodiment of blowers 80 do not need to be ceiling mounted, but the advantages of a closed passage 68 above the room ceiling is retained. Thus, and with particular reference to FIGS. 4, 5 and 6, the room 10 setup is like the FIG. 1, 2 embodiment with the same walls 12–18 located within the same hospital space as there described. Proceeding to the different aspects of this embodiment, the room 10 top wall 22 has a horizontal continued extent **22*a* which projects beyond the viewport 48. Wall 18 skirt 76 is likewise displaced as shown. This wall extent 22*a* is provided with a secondary outlet 88 whereby the closed passageway begins with the room outlet port O (opening 66) and ends with secondary outlet 88. A side mounted pair of blowers 80 is provided in cabinet 90, a generally rectangular structure which houses the blowers supported on framing 92, their inlets oriented to the perforate grill 94 of the cabinet and their outlets with baffles 96, oriented toward the plenum 62 between the HEPA filter bank 58 and hospital room wall 26. Blower operation is regulated through console controls 98. A series of prefilters 84 between the grill 94 and the blower intake 78 serve to filter gross particles, and may be provided with virustatic control agents as in the FIG. 1 embodiment. A cooling coil 100 for temperature control of the recirculating air is provided behind the prefilters 84**.

Figure 6:
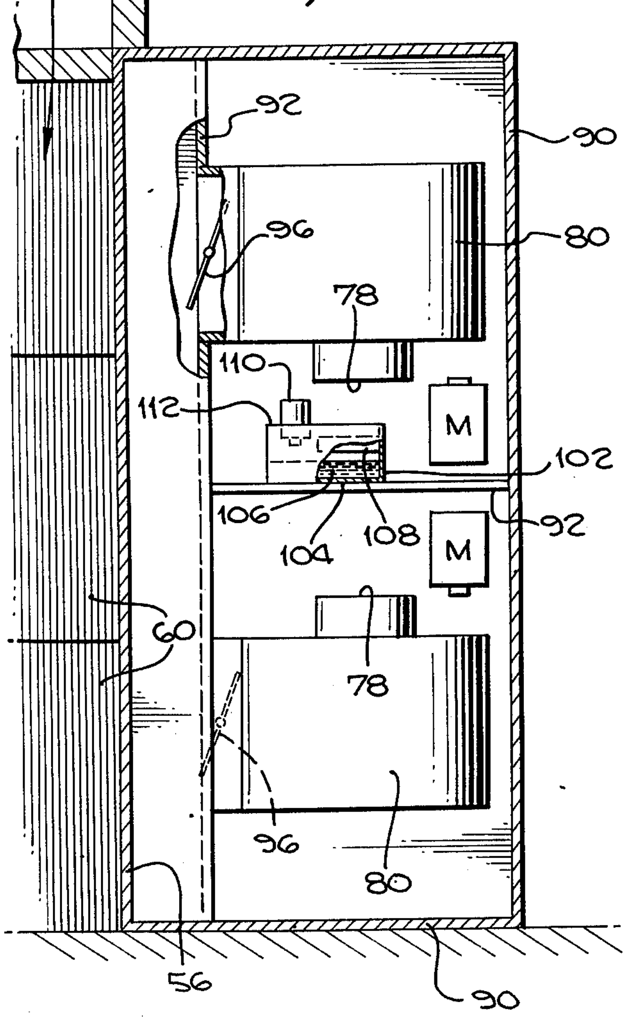
FIG. 6 is a view in vertical section taken on line 6—6 in FIG. 5.

With more particular reference to FIG. 6, there is shown a further innovation according to the invention. A conventional humidifier device is shown at 102 comprising a tank 104 for storing water 106. A heating coil 108 controllably evaporates water into the recirculating air to maintain a desired level of humidity, e.g. 50% for chemotherapy uses and 90% or more for burn victims. It has been observed that the stored water 106 is a fertile multiplying medium for bacteria and virus which once in the water may multiply drastically, ultimately to enter the room. This problem is obviated by provision herein of a virustatic control in the form of a metering container of liquid virustatic agent, e.g. one or more quaternary ammonium compounds, e.g. Control III, which are dripped into the stored water 106 at a predetermined rate from the inverted supply bottle 110 supported in place by the top wall 112 of tank 104.

While not forming per se a part of the present invention, this structure of the HEPA filters used herein comprise, with reference to FIGS. 7 and 8, reversely folded or accordion pleated fiberglass cloth 113 of high density, interleaved with spacers 114 which comprise fluted or corrugated aluminum or the like, to define a series of flow passages 116. The assembly of fiberglass cloth folds and aluminum spacers is tightly compressed and secured in a frame (not shown) to enable effective filtration of air containing contaminants as small as 0.3 micron with up to 99.97% efficiency. This level of filtration effectively removes bacteria, which are above 0.3 micron up to about 13 microns in size.

As noted, it is a further feature of the invention that destruction of virus-sized contaminants is provided. Thus virus which have a particle size typically 0.002 to 0.015 micron may be filtered by humidifying the air passing through the air flow loop, by the attachment of water droplets, effectively increasing the size of the virus to HEPA-filterable dimensions. In a further described features of the invention, prefilter 84 medium is coated with a virustatic material e.g. Control III (tradename), which is added in virustatically effective amounts into the humidifying water normally added to the air stream for patient comfort. It has been found that the addition of from 200 to 500 parts per million of the virustat, Control III, to the humidity water supply effectively controls virus levels.

We claim:

1. A patient isolation room having side, top and bottom wall means surrounding a relatively smaller patient locus adapted to be installed in a normal hospital room, one of said side walls defining a room entry doorway, said top wall having a horizontal continued extent projecting beyond said doorway-defining side wall, a horizontal air outlet formed in said top wall extent adjacent said sidewall and spaced from said doorway, further wall means between said patient isolation room top wall and the hospital room ceiling defining a closed passageway therebetween continuous air flow loop means isolating said locus from airborne contaminants beyond the locus, said loop means including an in-room inlet means and an in-room outlet means relatively sized and oppositely arranged in respective walls of said room such that said locus is encompassed on every side with a purified horizontal unidirectional, laminar air stream of uniform velocity throughout its cross-section, said in-room outlet means and said horizontal air outlet communicating with said closed passageway, and means including high efficiency particulate air filters for repurifying air and a blower alongside said doorway defining sidewall adjacent and below said horizontal air outlet thereby, being spaced from said doorway, said blower being in air drawing communication with said horizontal air outlet for recirculating air from said in-room outlet means, through said horizontal air outlet, and to said in-room inlet means, said loop means beyond said room conducting depurified air from said in-room outlet means, through said closed passage above the room top wall, through said horizontal outlet, into said blower therebelow, to and through said filters for repurifying and recirculating and into said in-room inlet means.

2. Patient isolation room according to claim 1 in which said patient locus is adjacent said in-room inlet means.

3. Patient isolation room according to claim 1 in which said in-room outlet means comprises a first wall port in a wall of said patient isolation room spaced above the plane of the room bottom wall and horizontally and vertically extended to receive said horizontal air streams traversing said patient locus.

4. Patient isolation room according to claim 3 in which said in-room inlet means comprises a second wall port in a side wall of said patient insolation room adjacent said patient locus in air filter communicating relation therewith, said second wall port and first wall port being respectively horizontally and vertically extended and opposed to each other to traverse the patient locus with a purified air stream dimensioned to continuously encompass said locus on all sides during passage between said in-room inlet means wall port and in-room outlet means wall port.

5. Patient isolation room according to claim 4 in which said first wall port is formed in a side wall of said patient isolation room and said second wall port is formed in a side wall opposite the first wall port to define the opposed relation of said in-room inlet means wall port and said in-room outlet means wall port.

6. Patient isolation room according to claim 5 in which said patient isolation room and the closed passage thereabove are relatively dimensioned to have a lower velocity air stream within said patient isolation room below said top wall then beyond said patient isolation room creating a relatively larger volume of air within the patient isolation room with respect to the closed passage thereabove and thereby, preventing room contamination from said passage through said room top wall.

7. Patient isolation room according to claim 4 in which said first wall port is formed in said top wall of said patient isolation room and said second inlet wall port is formed in a side wall thereof beyond the patient locus relative to said first outlet wall port to define the opposed relation of said in-room inlet means wall port and said in-room outlet means wall port.

8. Patient isolation room according to claim 7 in which said patient isolation room and said closed passage loop portion thereabove are relatively dimensioned to have a lower velocity air stream within said patient isolation room below said top wall than beyond said patient isolation room creating a relatively larger volume of air within the patient isolation room with respect to the closed passage thereabove and thereby, preventing room contamination from said passage through said room top wall.

9. Patient isolation room according to claim 4 in which said blower communicates negative pressure to said in-room outlet means wall port through said passage and positive pressure to said in-room inlet means wall port through said air filter.

* * * * *